US011130797B2

(12) United States Patent
Kazantsev et al.

(10) Patent No.: US 11,130,797 B2
(45) Date of Patent: *Sep. 28, 2021

(54) COVALENT MODIFICATION OF BIOLOGICAL MACROMOLECULES

(71) Applicant: Mosaic Biosciences, Inc., Boulder, CO (US)

(72) Inventors: Alexei Kazantsev, Boulder, CO (US); Peter D. Mariner, Superior, CO (US); Martin Stanton, Boulder, CO (US)

(73) Assignee: MOSAIC BIOSCIENCES, INC., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/971,700

(22) Filed: May 4, 2018

(65) Prior Publication Data
US 2018/0355019 A1    Dec. 13, 2018

Related U.S. Application Data

(63) Continuation of application No. 14/210,106, filed on Mar. 13, 2014, now Pat. No. 9,988,433.

(60) Provisional application No. 61/782,107, filed on Mar. 14, 2013.

(51) Int. Cl.
| *A01N 1/00* | (2006.01) |
| *C07K 14/75* | (2006.01) |
| *C12N 9/96* | (2006.01) |
| *C07K 1/107* | (2006.01) |
| *A61K 47/60* | (2017.01) |
| *A61K 47/54* | (2017.01) |
| *C12N 9/50* | (2006.01) |

(52) U.S. Cl.
CPC ............ *C07K 14/75* (2013.01); *A61K 47/557* (2017.08); *A61K 47/60* (2017.08); *C07K 1/1077* (2013.01); *C12N 9/63* (2013.01); *C12N 9/96* (2013.01); *C12Y 304/22006* (2013.01)

(58) Field of Classification Search
None
See application file for complete search history.

(56) References Cited

U.S. PATENT DOCUMENTS

| 3,920,877 | A | 11/1975 | Barber et al. |
| 4,081,598 | A | 3/1978 | Morgan et al. |
| 4,808,638 | A | 2/1989 | Steinkraus et al. |
| 4,969,998 | A | 11/1990 | Henn |
| 5,177,056 | A | 1/1993 | Hilti et al. |
| 5,399,624 | A | 3/1995 | Glaser et al. |
| 5,410,016 | A | 4/1995 | Hubbell et al. |
| 5,496,872 | A | 3/1996 | Constancis et al. |
| 5,730,601 | A | 3/1998 | Bowman et al. |
| 5,837,751 | A | 11/1998 | Jacobine et al. |
| 5,858,746 | A | 1/1999 | Hubbell et al. |
| 6,060,582 | A | 5/2000 | Hubbell et al. |
| 6,169,126 | B1 | 1/2001 | Szum et al. |
| 7,018,655 | B2 | 3/2006 | Lele et al. |
| 7,288,608 | B2 | 10/2007 | Bowman et al. |
| 7,744,912 | B1 | 6/2010 | Hubbell et al. |
| 7,842,667 | B2 | 11/2010 | Seliktar et al. |
| 8,519,086 | B2 | 8/2013 | Bowman et al. |
| 8,859,716 | B2 | 10/2014 | Bowman et al. |
| 9,631,092 | B2 | 4/2017 | Bowman et al. |
| 9,987,393 | B2 | 6/2018 | Anseth et al. |
| 9,988,433 | B2 * | 6/2018 | Kazantsev ........... A61K 47/557 |
| 10,016,505 | B2 * | 7/2018 | Mariner .................. A61L 27/54 |
| 10,189,952 | B2 | 1/2019 | Bowman et al. |
| 10,912,837 | B2 | 2/2021 | Kazantsev |
| 2002/0004537 | A1 | 1/2002 | Krongauz et al. |
| 2002/0076443 | A1 | 6/2002 | Stein et al. |
| 2004/0086479 | A1 | 5/2004 | Grinstaff et al. |

(Continued)

FOREIGN PATENT DOCUMENTS

| GB | 588018 A | 5/1947 |
| JP | 363280711 A | 11/1988 |

(Continued)

OTHER PUBLICATIONS

Benesch, R. et al. (1958). "Thiolation of Proteins," *Biochemistry* 44:848-853.

Canalle, L.A. et al. (2010). "Polypeptide-Polymer Bioconjugates," *Chem. Soc. Rev.* 39:329-353.

Claudino, M. et al. (2013). "Thiol-ene Coupling Kinetics of $_D$-Limonene: A Versatile 'Non-Click' Free-Radical Reaction Involving a Natural Terpene," *RSC Adv.* 3:11021-11034.

Espeel, P. et al. (Jan. 25, 2011). "One-Pot Multistep Reactions Based on Thiolactones: Extending the Realm of Thiol-Ene Chemistry in Polymer Synthesis," *Journal of the American Chemical Society* 133:1678-1681.

(Continued)

*Primary Examiner* — Hope A Robinson
(74) *Attorney, Agent, or Firm* — Morrison & Foerster LLP

(57) ABSTRACT

The present disclosure provides a method of covalently modifying a biological macromolecule, the method comprising subjecting a reaction mixture comprising: (a) a biological macromolecule comprising one or more thiol groups; and (b) a molecule comprising one or more olefin or alkyne moieties to a radical reaction under conditions sufficient to produce the covalently modified biological macromolecule. The present disclosure also provides a method of covalently modifying a biological macromolecule, the method comprising subjecting a reaction mixture comprising: (a) a molecule comprising one or more thiol groups; and (b) a biological macromolecule comprising one or more olefin or alkyne moieties to a radical reaction under conditions sufficient to produce the covalently modified biological macromolecule. The present disclosure further provides a covalently modified biological macromolecule prepared by any of the disclosed methods. The covalently modified biological macromolecules may be further crosslinked to form a scaffold.

15 Claims, 1 Drawing Sheet

(56) References Cited

U.S. PATENT DOCUMENTS

| | | |
|---|---|---|
| 2004/0091462 A1 | 5/2004 | Lin et al. |
| 2005/0244393 A1 | 11/2005 | Philippart et al. |
| 2006/0029578 A1 | 2/2006 | Hoemann et al. |
| 2006/0204582 A1 | 9/2006 | Stein et al. |
| 2007/0248567 A1 | 10/2007 | Pathak et al. |
| 2009/0311338 A1 | 12/2009 | Pathak et al. |
| 2009/0324720 A1 | 12/2009 | He et al. |
| 2010/0137510 A1 | 6/2010 | Seliktar et al. |
| 2010/0178355 A1 | 7/2010 | Hoemann et al. |
| 2010/0233246 A1 | 9/2010 | Sehl et al. |
| 2010/0291357 A1 | 11/2010 | Polizzotti et al. |
| 2010/0304338 A1 | 12/2010 | Cramer et al. |
| 2012/0225101 A1 | 6/2012 | Kao et al. |
| 2012/0202263 A1 | 8/2012 | Blakely et al. |
| 2012/0220542 A1* | 8/2012 | Barrack ............... A61P 27/02 514/21.3 |
| 2013/0197189 A1 | 8/2013 | Aimetti et al. |
| 2014/0038826 A1 | 2/2014 | Anseth et al. |
| 2014/0112960 A1 | 4/2014 | Lin |
| 2017/0247541 A1 | 8/2017 | Bowman et al. |
| 2018/0043030 A1* | 2/2018 | Kazantsev ............ C08G 81/00 |
| 2018/0360970 A1 | 12/2018 | Mariner et al. |

FOREIGN PATENT DOCUMENTS

| | | |
|---|---|---|
| RU | 2488863 C2 | 7/2013 |
| WO | WO-2009/039307 A2 | 3/2009 |
| WO | WO-2009/085902 A1 | 7/2009 |
| WO | WO-2012/103445 A2 | 8/2012 |
| WO | WO-2012/103445 A3 | 8/2012 |
| WO | 2012103445 A3 | 10/2012 |
| WO | WO-2013/116791 A1 | 8/2013 |
| WO | WO-2016/130573 A2 | 8/2016 |

OTHER PUBLICATIONS

Fairbanks, B.D. et al. (2009; e-pub. Sep. 23, 2009). "Photoinitiated Polymerization of PEG-Diacrylate with Lithium Phenyl-2,4,6-Trimethylbenzoylphasphinate: Polymerization Rate and Cytocompatibility," *Biomaterials* 30:6702-6707.

Northrop, B.H. et al. (2012). "Thiol-Ene Click Chemistry: Computational and Kinetic Analysis of the Influence of Alkene Functionality," *Journal of the American Chemical Society* 134:13804-13817.

Sawicki, L.A. et al. (Nov. 30, 2014). "Design of Thiol-Ene Photoclick Hydrogels Using Facile Techniques for Cell Culture Applications," *Biomaterials Science* 2(11):1612-1626.

Solomons, T.W.G. (1988). "Homolytic Bond Dissociation Energies and the Relative Stabilities of Free Radicals," in *Organic Chemistry* 1 $4^{th}$ edition, pp. 402-403, four pages.

U.S. Final Office Action dated Jan. 28, 2019, for U.S. Appl. No. 15/549,787, filed Aug. 9, 2017, 11 pages.

Anderson, S.B. et al. (May 2011). "The Performance of Human Mesenchymal Stem Cells Encapsulated in Cell-Degradable Polymer-peptide Hydrogels," *Biomaterials* 32(14):3564-3574.

Athanasiou, K.A. et al. (1996). "Sterilization, Toxicity, Biocompatibility and Clinical Applications of Polylactic Acid/Polyglycolic Acid Copolymers," *Biomaterials* 17(2):93-102.

Cadée, J.A. et al. (Jun. 5, 2000). "In Vivo Biocompatibility of Dextran-Based Hydrogels," *J Biomed Mater Res.* 50(3):397-404.

Chalker, J.M. et al. (Jul. 7, 2009, e-published on May 27, 2009). "Enabling Olefin Metathesis on Proteins: Chemical Methods for Installation of S-Allyl Cysteine," *Chem. Commun.* 25:3714-3716.

Conte, M.L. et al. (2011). "Multi-Molecule Reaction of Serum Albumin Can Occur Through Thiol-Yne Coupling," *Chemical Communications* 47:11086-11088.

Cramer, N.B. et al. (2003). "Thiol-Ene Photopolymerization Mechanism and Rate Limiting Step Changes for Various Vinyl Functional Group Chemistries," *Macromolecules* 36:7964-7969.

Dondoni, A. et al. (2009). "A New Ligation Strategy for Peptide and Protein Glycosylation: Photoinduced Thiol-Ene Coupling," *Chem. Eur.J.* 15:11444-11449.

Draye, J.-P. et al. (Sep. 1998). "In Vitro and in Vivo Biocompatibility of Dextran Dialdehyde Cross-linked Gelatin Hydrogel Films," *Biomaterials* 19(18):1677-1687.

Fairbanks, B.D. et al. (2009). "Thiol-Yne Photopolymerizations; Novel Mechanism, Kinetics, and Step-Growth Formation of Highly Cross-Linked Networks," *Macromolecules* 42:211-217.

Fairbanks, B.D. et al. (2010) "Reaction Rates and Mechanisms for Radical, Photoinitated Addition of Thiols to Alkynes, and Implications for Thiol-Yne Photopolymerizations and Click Reactions," *Macromolecules* 43:4113-4119.

Floyd, N. et al., (2009). "Thiyl Glycosylation of Olefinic Proteins: S-Linked Glycoconjugate Synthesis," *Angewandte Chemie. Int. Ed.* 48:7798-7802.

Fu, Y. et al. (Jan. 2012). "3D Cell Entrapment in Crosslinked Thiolated Gelatin-poly(ethylene glycol) Diacrylate Hydrogels," *Biomaterials* 33(1):48-58.

Fu, Y. et al., (Aug 2011). "In Situ Forming poly(ethylene glycol)-Based Hydrogels via Thiol-Maleimide Michael-Type Addition," *J. Biomed. Mater. Res. A* 98(2):201-211.

Gallez, B. et al. (Jul. 1998). "Small Particles of Fusinite and Carbohydrate Chars Coated with Aqueous Soluble Polymers: Preparation and Applications for In Vivo EPR Oximetry," *Magn Reson Med.* 40(1):152-159.

Geyer, U. et al. (1994). "Formation, Derivatization and Applications of Bacterial Cellulose," *Int. J. Biol. Macromol.* 16(6):343-347.

Hernandez, K. et al. (2011). "Control of Protein Immobilization: Coupling Immobilization and Site-Directed Mutagenesis to Improve Biocatalyst or Biosensor Performance," *Enzyme and Microbial Technology* 48:107-122.

Hoyle, C.E. et al. (2004). "Thiol-Enes: Chemistry of the Past with Promise for the Future" *Journal of Polymer Science: Part A: Polymer Chemistry* 42:5301-5338.

Jain, R.A. (2000). "The Manufacturing Techniques of Various Drug Loaded Biodegradable Poly(lactide-co-glycolide) (PLGA) Devices," *Biomaterials* 21:2475-2490.

Jin, R. et al. (Jun. 2010). "Synthesis and characterization of hyaluronic acid-poly(enthylene glycol) hydrogels via Michael addition: An injectable biomaterial for cartilage repair," *Acta Biomaterialia* 6(6):1968-1977.

Jones, M.W. et al. (2009). "Phosphine-Mediated One-Pot Thiol-Ene "Click" Approach to Polymer-Protein Conjugates," *Chem. Commun.*, 5272-5274.

Lee, S. et al. (2016 ; e-published on Nov. 23, 2015). "Fabrication of PEG-carboxymethylcellulose Hydrogel by Thiol-norbornene Photo-click Chemistry," *International Journal of Biological Macromolecules* 83:1-8.

Li, Y. et al., (2012). "Genetically Encoded Alkenyl-Pyrrolysine Analogues for Thiol-Ene Reaction Mediated Site-Specific Protein Labeling" *Chemical Science* 3:2766-2770.

Lin, C.C. et al. (2011) "PEG Hydrogels Formed by Thiol-Ene Photo-Click Chemistry and Their Effect on the Formation and Recovery of Insulin-Secreting Cell Spheroids" *Biomaterials* 32(36):9685-9695.

Lin, S.S. et al. (Aug. 30-Sep. 3, 2006). "Controlled Release of PRP-Derived Growth Factors Promotes Osteogenic Differentiation of Human Mesenchymal Stem Cells," *Proceedings of the $28^{th}$ IEEE EMBS Annual International Conference*, New York, USA, SaA06. 4:4358-4361.

Lowe, A.B. et al. (2010). "Thiol-yne Click Chemistry: A Powerful and Versatile Methodology for Materials Synthesis," *Journal of Materials Chemistry*, 20:4745-4750.

Maleimide, retrieved from <www.en.wikipedia.org/wiki/Maleimides> on Mar. 3, 2012, 3 pages.

McCall, J.D. et al. (2012) "Thiol-Ene Photopolymerizations Provide a Facile Method to Encapsulate Proteins and Maintain Their Bioactivity", *Biomacromolecules* 13:2410-2417.

Moreira, H. et al. (Feb. 2000). "Use of Bioresorbable Membrane (Sodium Hyaluronate + Carboxymethylcellulose) After Controlled Bowel Injuries in a Rabbit Model," *Diseases of the Colon Rectum* 43(2):182-187.

(56) References Cited

OTHER PUBLICATIONS

Qiu, B. et al. (2003). "A Hydrogel Prepared by in Situ Cross-Linking of a Thiol-Containing Poly(Ethylene Glycol)-Based Copolymer: A New Biomaterial for Protein Drug Delivery," *Biomaterials* 24:11-18.
Raza, A. et al. (2013). "The Influence of Matrix Degradation and Functional on Cell Survival and Morphogenesis in PEG-Based Hydrogels," *Macromolecular Bioscience* 13(8):1048-1058.
Roberts, J.J. et al. (2013). "Comparison of Photopolymerizable Thiol-ene PEG and Acrylate-based PEG Hydrogels for Cartilage Development," *Biomaterials* 34(38):9969-9979.
Roskos, K.V. et al. (1995). "Biocompatibility and in Vivo Morphine Diffusion into a Placebo Morphine-triggered Naltrexone Delivery Device in Rabbits," *Biomaterials* 16(16):1235-1239.
Russo, L. et al. (Mar. 2016; e-published on Dec. 9, 2015). "Gelatin Hydrogels via Thiol-ene Chemistry," *Monatshefte für Chemie* 147(3):587-592.
Sell, S.A. et al. (Dec. 2012; e-published on Sep. 25, 2012) "The Incorporation and Controlled Release of Platlet-Rich Plasma-Derived Biomolecules From Polymeric Tissue Engineering Scaffolds," *Polym. Int.* 61(12):1703-1709.
Veronese, F.M. (2001) "Peptide and Protein PEGylation: A Review of Problems and Solutions", *Biomaterials* 22:405-417.
Wiese, K.G. (1993). "Osmotically Induced Tissue Expansion with Hydrogels: A New Dimension in Tissue Expansion? A Preliminary Report," *Journal of Cranio-Maxillo-Facial Surgery* 21:309-313.
Wu, J.-T. et al. (2012) "Reactive Polymer Coatings: A General Route t Thiol-ene and Thiol-yne Click Reactions" Macromol. *Rapid Commun.* 33:922-927.
Xiang, Z. et al. (Sep. 2013; e-published on Aug. 4, 2013). "Adding an Unnatural Covalent Bond to Proteins Through Proximity-enhanced Bioreactivity," *Nature Methods* 10(9):885-888 (also includes the Erratum—Corrected after Print on Nov. 21, 2013).
Yan, J. et al. (Oct. 8, 2013). "Growing Hyperbranched Polymers Using Natural Sunlight," *Scientific Reports* 3(2841):1-7.
European Office Action for Application 13743245.6 dated Jan. 18, 2017, 5 pages.
European Supplementary Search Report dated Dec. 14, 2015, for European Patent Application No. 13743245.6, filed on Feb. 1, 2013, 11 pages.
International Preliminary Report on Patentability dated Aug. 24, 2017, for PCT/US2016/017189, filed on Feb. 9, 2016, 8 pages.
International Preliminary Report on Patentability dated Aug. 8, 2013 for PCT Patent Application No. PCT/US2012/022920, filed on Jan. 27, 2012, 8 pages.
International Search Report and Written Opinion dated Aug. 30, 2012, for PCT Patent Application No. PCT/US2012/022920, Internationally filed on Jan. 27, 2012, 9 pages.
International Search Report dated Apr. 11, 2013 for PCT Patent Application No. PCT/US2013/024520 filed on Feb. 1, 2013, three pages.
International Search Report dated Aug. 18, 2016, for PCT Patent Application No. PCT/US2016/17189, Internationally filed on Feb. 9, 2016, 4 pages.
International Search Report dated Jan. 3, 2003, for PCT Patent Application No. PCT/US02/32669, filed Oct. 10, 2002, 1 page.
Written Opinion dated Apr. 11, 2013 for PCT Patent Application No. PCT/US/13/24520 filed on Feb. 1, 2013, 6 pages.
Written Opinion dated Aug. 18, 2016, for PCT Patent Application No. PCT/US2016/17189, Internationally filed on Feb. 9, 2016, 6 pages.
Written Opinion dated Aug. 30, 2012, for PCT Application No. PCT/US2012/022920, filed on Jan. 27, 2012, 6 pages.
Non-Final Office Action dated Dec. 31, 2015, for U.S. Appl. No. 13/758,942, filed Feb. 4, 2013, 14 pages.
U.S. Final Office Action dated Jan. 29, 2016, for U.S. Appl. No. 14/210,106, filed Mar. 13, 2014, 11 pages.
U.S. Final Office Action dated Jun. 5, 2006, for U.S. Appl. No. 10/269,916, filed Oct. 10, 2002, 7 pages.
U.S. Final Office Action dated Jun. 29, 2017, for U.S. Appl. No. 14/210,106, filed Mar. 13, 2014, 14 pages.
U.S. Final Office Action dated Mar. 10, 2009, for U.S. Appl. No. 11/858,062, filed Sep. 19, 2007, 6 pages.
U.S. Final Office Action dated May 31, 2011, for U.S. Appl. No. 12/556,640, filed Sep. 10, 2009, 5 pages.
U.S. Final Office Action dated Nov. 30, 2015, for U.S. Appl. No. 13/981,885, filed Oct. 9, 2013, 17 pages.
U.S. Final Office Action dated Oct. 3, 2016, for U.S. Appl. No. 13/758,942, filed Feb. 4, 2013, 11 pages.
U.S. Final Office Action dated Sep. 14, 2012, for U.S. Appl. No. 12/556,640, filed Sep. 10, 2009, 10 pages.
U.S. Non Final Office Action dated Jul. 16, 2015, for U.S. Appl. No. 14/210,106, filed Mar. 13, 2014, 10 pages.
U.S. Non Final Office Action dated May 8, 2015, for U.S. Appl. No. 14/485,490, filed Sep. 12, 2014, 10 pages.
U.S. Non Final Office Action dated Apr. 3, 2015, for U.S. Appl. No. 13/981,885, filed Oct. 9, 2013, 16 pages.
U.S. Non Final Office Action dated Aug. 6, 2008, for U.S. Appl. No. 11/858,062, filed Sep. 19, 2007, 6 pages.
U.S. Non Final Office Action dated Dec. 30, 2005, for U.S. Appl. No. 10/269,916, filed Oct. 10, 2002, 6 pages.
U.S. Non Final Office Action dated Jul. 18, 2016, for U.S. Appl. No. 13/981,885, filed Oct. 9, 2013, 18 pages.
U.S. Non Final Office Action dated May 19, 2016, for U.S. Appl. No. 14/848,141, filed Sep. 8, 2015, 12 pages.
U.S. Non Final Office Action dated Nov. 20, 2013, for U.S. Appl. No. 13/951,268, filed Jul. 25, 2013, 9 pages.
U.S. Non Final Office Action dated Oct. 25, 2010, for U.S. Appl. No. 12/556,640, filed Sep. 10, 2009, 9 pages.
U.S. Non Final Office Action dated Sep. 16, 2016, for U.S. Appl. No. 14/210,106, filed Mar. 13, 2014, 12 pages.
U.S. Non Final Office Action dated Nov. 1, 2017, for U.S. Appl. No. 15/409,392, filed Jan. 18, 2017, 19 pages.
U.S. Notice of Allowance dated Dec. 16, 2016 for U.S. Appl. No. 14/848,141, filed Sep. 8, 2015, 7 pages.
U.S. Notice of Allowance dated Apr. 26, 2013, for U.S. Appl. No. 12/556,640, filed Sep. 10, 2009, 6 pages.
U.S. Notice of Allowance dated Dec. 14, 2006, for U.S. Appl. No. 10/269,916, filed Oct. 10, 2002, 6 pages.
U.S. Notice of Allowance dated Jun. 11, 2014, for U.S. Appl. No. 13/951,268, filed Jul. 25, 2013, 13 pages.
U.S. Notice of Allowance dated Jun. 19, 2007, for U.S. Appl. No. 10/269,916, filed Oct. 10, 2002, 6 pages.
U.S. Notice of Allowance dated Oct. 20, 2017, for U.S. Appl. No. 14/210,106, filed Mar. 13, 2014, 11 pages.
U.S. Non Final Office dated Apr. 10, 2018, for U.S. Appl. No. 14/210,106, filed Mar. 13, 2014, 14 pages.
U.S. Notice of Allowance dated Apr. 16, 2018, for U.S. Appl. No. 14/210,106, filed Mar. 13, 2014, 12 pages.
U.S. Restriction Requirement dated Feb. 12, 2015, for U.S. Appl. No. 14/210,106, filed Mar. 13, 2014, 6 pages.
U.S. Restriction Requirement dated Aug. 31, 2015 for U.S. Appl. No. 13/758,942, filed Feb. 4, 2013, 8 pages.
U.S. Restriction Requirement dated Jul. 13, 2005, for U.S. Appl. No. 10/269,916, filed Oct. 10, 2002, 9 pages.
U.S. Restriction Requirement dated Jul. 14, 2017, for U.S. Appl. No. 15/409,392, filed Jan. 18, 2017, 10 pages.
U.S. Restriction Requirement dated Nov. 20, 2014 for U.S. Appl. No. 13/981,885, filed Oct. 9, 2013, 11 pages.
U.S. Restriction Requirement dated Sep. 13, 2005, for U.S. Appl. No. 10/269,916, filed Oct. 10, 2002, 5 pages.
U.S. Appl. No. 15/973,163, filed May 7, 2018, by Mariner et al. (Copy not submitted herewith pursuant to the waiver of 37 C.F.R. § 1.98(a)(2)(iii) issued by the Office on Sep. 21, 2004.).
Lowe A.B. (2010). "Thiol-ene "click" Reactions and Recent Applications in Polymer and Materials Synthesis," Polym. Chem. 1(1):17-36.
Pfeifer C. S. et al. (Jul. 7, 2011). "Delayed Gelation Through Chain-Transfer Reactions: Mechanism for Stress Reduction in Methacrylate Networks." Polymer 52(15):3295-3303, 21 pages.

(56) References Cited

OTHER PUBLICATIONS

Lowe A.B. (2014). "Thiol-ene "click" Reactions and Recent Applications in Polymer and Materials Synthesis: A First Update," Polym. Chem. 5:4820-4870.

U.S. Final Office Action dated Mar. 20, 2020, for U.S. Appl. No. 15/549,787, filed Aug. 9, 2017, 8 pages.

Wutticharoenwong, K. (Dec. 2007). "Bio-Based Reactive Diluents and Thiol-ene Photopolymerization for environmentally Benign Coatings," Dissertation presented to the Graduate Faculty of the University of Akron, 228 pages.

U.S. Appl. No. 17/085,798, filed Oct. 30, 2020, by Alexei Kazantsev et al. (A copy of the U.S. Patent Application is not submitted herewith pursuant to the waiver of 37 C.F.R. § 1.98(a)(2)(iii) issued by the Office on Sep. 21, 2004.).

* cited by examiner

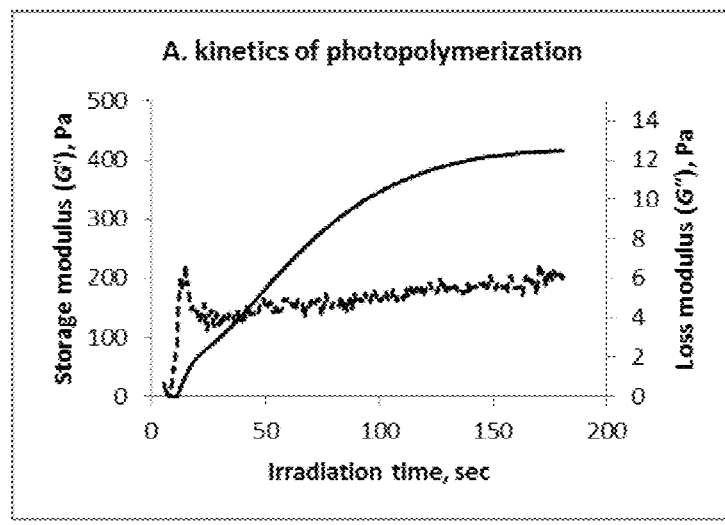
B. Hydrogels before and after treatment with PBS or trypsin
Hydrogels before trypsin treatment
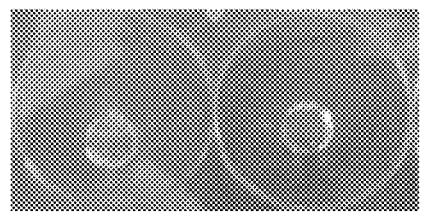
Treatment for 3 hrs 30 min at 37°C
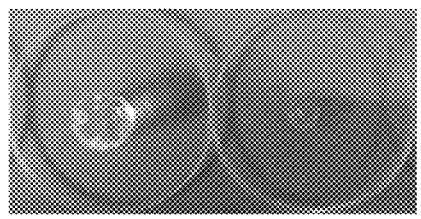
PBS        Trypsin

COVALENT MODIFICATION OF BIOLOGICAL MACROMOLECULES

CROSS REFERENCE TO RELATED APPLICATIONS

This application is a continuation of U.S. patent application Ser. No. 14/210,106, filed Mar. 13, 2014, now U.S. Pat. No. 9,988,433, which claims priority benefit to U.S. Provisional Patent Application No. 61/782,107, filed Mar. 14, 2013, the contents of which are hereby incorporated herein by reference in their entirety.

BACKGROUND OF THE INVENTION

Covalent modification of proteins and other biological macromolecules (carbohydrates, proteoglycans, nucleic acids etc.) is widely used in numerous applications of modern-day biotechnology and academic science. The goals typically sought after by such modifications are to extend the chemical, structural and functional repertoire of the biological macromolecule of interest in order to conform the macromolecule to the requirements of a specific application while retaining or extending its inherent functional properties. Examples include covalent incorporation of proteins into polymeric networks for a variety of tissue engineering applications; manipulation of pharmacokinetics and pharmacodynamics of therapeutic proteins by site-specific attachment of polymeric chains (e.g. polyethylene glycol); covalent attachment of proteins to solid support such as surfaces and beads of variable sizes for a plethora of analytical and enrichment applications; covalent attachment of proteins to various drugs, therapeutics, nanoparticles and various nano-scale biosensors in order to improve solubility, biocompatibility, achieve targeting to a specific organ or tissue and influence other pharmacokinetic and pharmacodynamics properties of such entities; covalent crosslinking of proteins to other proteins or non-protein tags (biotin, antibody, DNA or RNA aptamer, receptor or its ligand, chromophores such as GFP and its relatives, dyes: fluorescent or not, fluorescence quenchers, quantum dots, and numerous others) in order to create chimeric macromolecules combining two or more otherwise (biologically) distinct functions in one molecule (e.g. specific enzymatic activity or fluorescence and a high affinity and specificity towards a certain analyte: used as chromogenic and fluorescent detectors in numerous ELISA and array-based applications).

Due to limited stability and solubility in organic solvents, biomacromolecules such as proteins typically have to be dissolved in water-based media in order to be covalently modified with reasonable efficiency. In proteins, naturally occurring chemical moieties capable of participating in non-enzymatic covalent crosslinking under aqueous environment are limited to a handful of ionizable residues, including amine-containing groups (unmodified amino-termini; side chains of lysines, arginines and histidines), thiols (side chains of cysteines), carboxylates (side chains of aspartates and glutamates) and phenolic side chains of tyrosines. Certain post-translational modifications occurring naturally in some proteins offer additional chemistries for covalent modifications, for example, glycoside residues in glycosylated proteins can be oxidized to form highly reactive aldehyde moieties.

Chemical transformations of the said residues in proteins typically involve nucleophile-mediated mechanisms (see, for example, Hermanson, G. T. Bioconjugate Techniques. $2^{nd}$ Edition. Elsevier Inc. 2008. ISBN: 978-0-12-370501-3), which imposes certain limitations on the types of chemistry that can be performed on a protein of interest. For example, the ionization state of the chemical group (e.g. amine) is coupled to its strength as a nucleophile, with protonated, positively charged amine being less reactive than non-protonated form. Such protonation state of a protein residue of interest can be controlled by maintaining appropriate pH in aqueous environment, for example by incorporation of appropriate buffer. However, because proteins are polyelectrolytes, certain physical properties of proteins, such as solubility, are also pH-dependent and, to a first approximation, are a function of the amino acid sequence of the specific protein. Therefore, certain proteins are unreactive under the pH optimal for their solubility, and vice versa. One example of such behavior is exhibited by Type I collagen, which in its native form is soluble only under a low pH that renders lysine side chains essentially unreactive.

Covalent attachment to the proteins of hydrophilic polymers such as poly(ethylene glycol) (PEG) (PEGylation) is widely used in biotechnological and biomedical applications as a way to increase solubility, to modulate pharmacokinetic and pharmacodynamics properties and to introduce additional, non-natural chemistries for further modifications. Typically this is accomplished through amine-reactive PEGylations. For example, see Francesco M Veronese (2001) Peptide and protein PEGylation: a review of problems and solutions, Biomaterials Volume 22, Issue 5, 1 Mar. 2001, Pages 405-417.

In another example, in U.S. Pat. No. 7,842,667 and US2010/0137510 A1 Seliktar and colleagues teach of attaching acrylated PEG moieties to collagen and fibrinogen in order to generate water-soluble, biodegradable telechelic macromers that can undergo subsequent chain-growth photopolymerization to yield biocompatible scaffolds for tissue engineering. This was achieved by subjecting denatured proteins to Michael-type addition reactions between acrylate moieties attached to PEG and thiol moieties contained by the proteins. The thiols were introduced into fibrinogen by reducing disulfide bridges that were naturally occurring in this protein; the collagen, naturally devoid of cysteine residues, was treated with a thiolating agent under highly denaturing conditions prior to the Michael addition. While PEGylated proteins obtained in such way were indeed more soluble than their precursors, the chemistries involved significantly limit the range of potential applications. For example, Michael addition used to obtain telechelic derivatives can be slow and require control over the pH of the media, which leads to increase in production costs. In turn, acrylate residues introduced by PEGylation with PEG-diacrylate (or its branched, multi-arm versions) undergo subsequent polymerization via a chain-growth mechanism, resulting in products with (potentially) undesirable pharmacokinetic properties (kinetic chains can easily exceed renal exclusion limit). The ability of acrylates to undergo homopolymerization also prohibits the use of a faster, pH-independent radical chemistry for the protein modification in this case.

Therefore, there is a need for simple, efficient, selective, and broadly applicable methods for the covalent modification of proteins.

Thiol-ene reactions are photochemically initiated, free-radical processes that take place between thiols and olefins (enes) via a sequential propagation/chain-transfer processes. Thiol-ene reactions have a number of significant and unique advantages that make them particularly beneficial. These benefits include the ability to photoinitiate the sample without any need for a distinct and possibly cytotoxic initiator species, the ability to process extremely thick (more than 30 cm) samples because of a self-eliminating light intensity gradient, the very low radical concentration present during reaction producing little protein damage from the free radicals, the lack of oxygen inhibition and the ease with which reactants of significantly varying chemistry can be covalently crosslinked. In addition, by virtue of their radical mechanisms, thiol-ene reactions are practically insensitive to the pH of the solution, which makes them ideally suited for protein modifications in a very broad sense: any protein containing appropriate reactive moieties (e.g. thiols, enes) can be covalently modified at any suitable moiety.

Photo-initiated thiol-ene chemistries have been used with limited success in a number of cases for covalent protein modification. Typically, a thiol-containing protein is subjected to a photo-initiated thiol-ene reaction with an ene-containing moiety, such as a synthetic sugar or polymer (PEG) containing an ene moiety (Conte M. L. et al. (2011). Chem. Commun. 47, pp. 11086-11088; Dondoni A. et al. (2009). Chem. Eur. J. 15, pp. 11444-11449). Alternatively, an ene functionality for subsequent thiol-ene reaction can be introduced into the protein by recombinant techniques, such as codon reprogramming (Floyd N. et al. (2009). Angew. Chem. Int. Ed. 48, pp. 7798-7802) or direct chemical modification of a reduced cysteine moiety (Chalker J. M. et al. (2009) Chem. Commun., pp. 3714-3716). The approaches described in the aforementioned examples have a number of significant limitations. First, codon reprogramming techniques typically are applicable to only small, well-soluble proteins to furnish one or two modifications per protein because recombinant proteins with higher number of unnatural residues are typically not expressed at high enough level (Li Y. et al. (2012) Chem. Sci. 3, pp 2766-2770). A larger number of reactive moieties are often needed to be introduced into proteins of variable, often large size, for a variety of biomedical applications, such as generation of cellular scaffolds for tissue engineering. Second, due to the chemical nature of the ene moieties involved, the above photo-induced thiol-ene reactions are relatively slow and require elevated concentrations of initiator and prolonged exposure of proteins to the UV light which often leads to unwanted side reactions, such as thiol-ene coupling to cystine residues (S—S bonds) that are important for structural integrity of certain proteins (Conte M. L. et al. (2011). Chem. Commun. 47, pp. 11086-11088; Dondoni A. et al. (2009). Chem. Eur. J. 15, pp. 11444-11449). Third, the long exposure can lead to free-radical induced damage of the protein. For example, in Li et al. (2012) the reaction time was up to 2 hours and resulted only in 50% yield of conjugated protein. Dondoni et al. (2009) were able to decrease reaction time to 5 minutes by elevating concentration of radical species in the course of transformation, however this resulted in unforeseen modification of cystine residues due to side reactions. Acrylate and methacrylate moieties, such as the ones employed in the applications U.S. Pat. No. 7,842,667 and US2010/0137510 A1, can undergo photo-initiated thiol-ene coupling more readily and thus alleviate some of the aforementioned limitations, but these electron-poor ene moieties tend to readily self-react (homopolymerize) in parallel with thiol-ene process (Cramer N. B. et al. (2003) Macromolecules 36, pp. 7964-7979) which significantly limits their chemical orthogonality.

It would be desirable to have methods and compositions that are rapid, pH independent, do not require harsh conditions, and where the functional groups do not self-react.

BRIEF SUMMARY

The present disclosure relates generally to methods for the covalent modification of biological macromolecules. More specifically, the present disclosure provides methods of covalently modifying proteins and other biological macromolecules using thiol-ene and thiol-yne chemistries. In a particular embodiment, the present disclosure provides methods of covalently modifying proteins and other biological macromolecules using thiol-ene chemistries with click-like properties and rapid reaction rates. The present disclosure also provides further practical applications of such covalently modified biological macromolecules, such as proteins. The present disclosure also provides the covalently modified biological macromolecules prepared by any of the methods disclosed herein.

In one aspect, the present disclosure provides a method of covalently modifying a biological macromolecule, the method comprising subjecting a reaction mixture comprising:

(a) a biological macromolecule comprising one or more thiol groups; and (b) a molecule comprising one or more olefin or alkyne moieties to a radical reaction under conditions sufficient to produce the covalently modified biological macromolecule. In a particular embodiment, the method comprises subjecting a reaction mixture comprising: (a) a biological macromolecule comprising one or more thiol groups; and (b) a molecule comprising one or more olefin moieties possessing click-like properties to a radical reaction under conditions sufficient to produce the covalently modified biological macromolecule. In specific embodiments, the olefin moiety is a norbornene or a vinyl ether derived olefin moiety (e.g., the olefin moiety comprises a norbornene or vinyl ether moiety). In other embodiments, the reaction is essentially complete in <10 min, <5 min, <2 min, and <1 min. In one embodiment, the olefin moiety comprises a norbornene or a vinyl ether moiety and the reaction is essentially complete within 10 or 5 or 2 or 1 minutes of radical initiation. In some embodiments, the biological macromolecule is a protein. In some embodiments, the radical reaction is a photoinitiated radical reaction. In some embodiments, the radical reaction is performed under non-denaturing conditions. In some embodiments, the biological macromolecule comprises one or more lysine side chains, and wherein the one or more thiol groups are introduced into the biological macromolecule by converting the one or more lysine side chains into the one or more thiol groups. In some embodiments, the one or more thiol groups are introduced into the biological macromolecule by site directed mutagenesis. In some embodiments, the biological macromolecule comprises one or more disulfide bonds, and wherein the one or more thiol groups are introduced into the biological macromolecule by converting the one or more disulfide bonds into the one or more thiol groups. In some embodiments, the one or more olefin or alkyne moieties further comprise one or more groups selected from the group consisting of poly(lactic acid) (PLA), polyglycolide (PGA), copolymer of PLA and PGA (PLGA), poly(vinyl alcohol) (PVA), poly(ethylene glycol) (PEG), poly(ethylene oxide), poly(ethylene oxide)-co-poly (propylene oxide) block copolymer (poloxamers, meroxapols), poloxamine, polyanhydride, polyorthoester, poly(hydroxy acid), polydioxanone, polycarbonate, polyaminocarbonate, poly(vinyl pyrrolidone), poly(ethyl oxazoline), carboxymethyl cellulose, hydroxyalkylated cellulose, hydroxyethyl cellulose, and methylhydroxypropyl cellulose. In one embodiment, the one or more olefin moieties further comprise or are incorporated into or onto one or more groups selected from the group consisting of poly (lactic acid) (PLA), polyglycolide (PGA), copolymer of PLA and PGA (PLGA), poly(vinyl alcohol) (PVA), poly (ethylene glycol) (PEG), poly(ethylene oxide), poly(ethylene oxide)-co-poly(propylene oxide) block copolymer (poloxamers, meroxapols), poloxamine, polyanhydride, polyorthoester, poly(hydroxy acid), polydioxanone, polycarbonate, polyaminocarbonate, poly(vinyl pyrrolidone), poly (ethyl oxazoline), carboxymethyl cellulose, hydroxyalkylated cellulose, hydroxyethyl cellulose, and methylhydroxypropyl cellulose. In some embodiments, the one or more olefin or alkyne moieties further comprises one or more groups selected from the group consisting of polypeptide, polysaccharide, carbohydrate, polysucrose, hyaluranic acid, dextran, dextran derivative, heparan sulfate, chondroitin sulfate, heparin, and alginate. In one embodiment, the one or more olefin moieties further comprise or are incorporated into or onto one or more groups selected from the group consisting of polypeptide, polysaccharide, carbohydrate, polysucrose, hyaluranic acid, dextran, dextran derivative, heparan sulfate, chondroitin sulfate, heparin, and alginate. In some embodiments, the one or more olefin or alkyne moieties further comprises one or more groups selected from the group consisting of gelatin, collagen, albumin, ovalbumin, fibrinogen, fibrin, laminin, fibronectin, vitronectin, fluorescent protein, green fluorescent protein, fluorescent dye, non-fluorescent dye, fluorescence quencher, polypeptide tag, His-tag, FLAG-tag, antibody, antibody fragment, nucleic acid aptamer, oligonucleotide and polynucleotide, ribonucleoprotein, and viral capsids. In one embodiment, the one or more olefin moieties further comprise or are incorporated into or onto one or more groups selected from the group consisting of gelatin, collagen, albumin, ovalbumin, fibrinogen, fibrin, laminin, fibronectin, vitronectin, fluorescent protein, green fluorescent protein, fluorescent dye, non-fluorescent dye, fluorescence quencher, polypeptide tag, His-tag, FLAG-tag, antibody, antibody fragment, nucleic acid aptamer, oligonucleotide and polynucleotide, ribonucleoprotein, and viral capsids. In some embodiments, the biological macromolecule is fibrinogen. In some embodiments, the biological macromolecule is chymopapain.

The present disclosure further provides a method of covalently modifying a biological macromolecule, the method comprising subjecting a reaction mixture comprising:
 (a) a molecule comprising one or more thiol groups; and
 (b) a biological macromolecule comprising one or more olefin or alkyne moieties
to a radical reaction under conditions sufficient to produce the covalently modified biological macromolecule. In one embodiment the present disclosure provides a method of covalently modifying a biological macromolecule, the method comprising subjecting a reaction mixture comprising: (a) a molecule comprising one or more thiol groups; and (b) a biological macromolecule comprising one or more olefin moieties with click-like properties to a radical reaction under conditions sufficient to produce the covalently modified biological macromolecule. In other embodiments, the reaction is essentially complete in <10 min, <5 min, <2 min, and <1 min. In one embodiment, the biological macromolecule comprising one or more olefin moieties comprises one or more norbornene or vinyl ether moieties and the reaction is essentially complete within 10 or 5 or 2 or 1 minutes of radical initiation. In some embodiments, the one or more thiol moieties further comprise or are incorporated into or onto one or more groups selected from the group consisting of poly(lactic acid) (PLA), polyglycolide (PGA), copolymer of PLA and PGA (PLGA), poly(vinyl alcohol) (PVA), poly(ethylene glycol) (PEG), poly(ethylene oxide), poly(ethylene oxide)-co-poly(propylene oxide) block copolymer (poloxamers, meroxapols), poloxamine, polyanhydride, polyorthoester, poly(hydroxy acid), polydioxanone, polycarbonate, polyaminocarbonate, poly(vinyl pyrrolidone), poly (ethyl oxazoline), carboxymethyl cellulose, hydroxyalkylated cellulose, hydroxyethyl cellulose, and methylhydroxypropyl cellulose. In some embodiments, the one or more thiol moieties further comprise or are incorporated into or onto one or more groups selected from the group consisting of polypeptide, polysaccharide, carbohydrate, polysucrose, hyaluranic acid, dextran, dextran derivative, heparan sulfate, chondroitin sulfate, heparin, and alginate. In some embodiments, the one or more thiol moieties further comprise or are incorporated into or onto one or more groups selected from the group consisting of gelatin, collagen, albumin, ovalbumin, fibrinogen, fibrin, laminin, fibronectin, vitronectin, fluorescent protein, green fluorescent protein, fluorescent dye, non-fluorescent dye, fluorescence quencher, polypeptide tag, His-tag, FLAG-tag, antibody, antibody fragment, nucleic acid aptamer, oligonucleotide and polynucleotide, ribonucleoprotein, and viral capsids. In some embodiments, the biological macromolecule is a protein. In some embodiments, the radical reaction is a photoinitiated radical reaction. In some embodiments, the radical reaction is performed under non-denaturing conditions. In some embodiments, the biological macromolecule is fibrinogen. In some embodiments, the biological macromolecule is chymopapain.

The present disclosure also provides the covalently modified biological macromolecule prepared according to any of the methods disclosed herein.

DESCRIPTION OF THE FIGURES

FIG. 1 depicts the covalent incorporation of bovine fibrinogen into polymeric scaffold. FIG. 1A shows the kinetics of the photopolymerization. FIG. 1B shows the visual appearance of fibrinogen-based hydrogels before and after treatment with PBS (negative control) or trypsin.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Here we disclose that favorable thiol-ene reaction and product attributes can be met by using ene containing moieties that are efficient at participating in thiol-ene reactions, but only undergo slow self-reaction. That is, the methods described herein are rapid, pH independent, do not require harsh conditions and use starting materials that reduce or eliminate self-reactivity, resulting in products that could not be obtained by other methods and/or chemistries that are more efficient than other methods, resulting in a lower incidence of unwanted side products or damage to a biological macromolecule due to prolonged exposure to high levels of free radicals. Thus, in one aspect of the methods, starting materials to a thiol-ene reaction are employed that are not susceptible to homopolymerization under free radical reaction conditions. In a particular variation, starting materials to a thiol-ene reaction are employed that are not susceptible to homopolymerization under free radical reaction conditions and which efficiently react (e.g., within 30 minutes or 20 minutes or 10 minutes or 5 minutes or one minute) with thiol moieties (e.g., on a biological macromolecule) under free radical reaction conditions. Chemistries that meet these general attributes are sometimes referred to as click chemistries. Moieties that possess such properties are referred to herein as possessing click-like properties. In one embodiment, the ene starting material of a thiol-ene reaction contains ene-moieties derived from norbornene or vinyl ether, both of which possess these click properties and react quickly enough such that free radical damage to the biological macromolecule being modified is not significant. Norbornene and vinyl ether moieties, due to their unusually high reactivity and specificity towards thiols under radical-mediated conditions are ideally suited for biological macromolecule (e.g., protein) modifications by photo-initiated thiol-ene chemistry. Upon initiation by a photo-induced, radical-mediated process, norbornene and vinyl ether residues readily and selectively react with thiols. The reaction proceeds at a very low transient concentration of radical species, requires a low dose of light and initiator and does not lead to notable damage to proteins due to side reactions (McCall J. D. and Anseth K. S. (2012) *Biomacromolecules* 13, pp. 2410-2417). Here we disclose that norbornene- and vinyl-ether mediated photoinitiated thiol-ene coupling can be applied to covalent modification of biological macromolecules such as proteins under a broad variety of biophysical conditions to expand chemical, biological and biophysical repertoire of biological macromolecules such as proteins as sought by biotechnological and biomedical applications. In one example provided below, the reaction is essentially complete in 3 minutes. In other embodiments, the reaction is essentially complete in <10 minutes, <5 minutes, <2 minutes and <1 minute following radical initiation (e.g., photoinitiation). The methods disclosed herein represent an advancement over prior chemistries in that, while prior methods are capable of carrying out a thiol-ene reaction, the moieties utilized in the prior art starting materials (acrylates, methacrylates and allyls) are either capable of self-reaction (homopolymerization) or react only very slowly and are thus inefficient for biotechnological and biomedical applications and/or are susceptible to production of unwanted side-products.

We further disclose that proteins or other macromolecules that have been derivatized using monomers that contain 2 or more click capable ene moieties can be then be used to efficiently form a three-dimensional polymer network when reacted with a second crosslinking moiety that contains 2 or more thiol containing groups. In some cases, it is desirable that the macromolecules be derivatized by attaching 3 or more of such ene containing moieties such that a fully crosslinked three-dimensional polymer network will be formed. In some embodiments, these three-dimensional polymer networks can be used as scaffolds for tissue regeneration.

The present disclosure provides simple, efficient, selective, and broadly applicable methods for the covalent modification of biological macromolecules. More specifically, the present disclosure provides methods of covalently modifying proteins and other biological macromolecules using thiol-ene and thiol-yne chemistries. In one embodiment, the present disclosure provides methods of covalently modifying proteins and other biological macromolecules using thiol-ene chemistries with click-like properties and rapid reaction rates. The present disclosure also provides further practical applications of such covalently modified biological macromolecules, such as proteins.

Thiol-ene and thiol-yne reactions are photochemically initiated, free-radical processes that take place between thiols and olefins (enes) or between thiols and alkyne containing moieties (ynes) via a sequential propagation/chain-transfer processes. Thiol-ene and thiol-yne reactions have a number of significant and unique advantages that make them particularly beneficial. In specific implementations, these benefits include the fast rate of these chemical transformations, the ability to photoinitiate the sample without any need for a distinct (and possibly cytotoxic) initiator species, the ability to process extremely thick (more than 30 cm) samples because of a self-eliminating light intensity gradient, the very low radical concentration present during reaction producing little protein damage from the free radicals, the lack of oxygen inhibition and the ease with which reactants of significantly varying chemistry can be covalently crosslinked. Further, important properties of these reactions include high efficiency and selectively: thiol-ene and thiol-yne reactions under appropriate conditions can proceed to completion in under one minute with little side reactivity. In addition, by virtue of their radical mechanisms, thiol-ene and thiol-yne reactions are practically insensitive to the pH of the solution, which makes them ideally suited for protein modifications in a very broad sense: any protein containing appropriate reactive moieties (e.g. thiols, enes or ynes) can be covalently modified at any suitable moiety. Applications of the thiol-ene chemistry to generate biodegradable materials for biomedical applications are disclosed in U.S. Pat. No. 7,288,608. Applications of the thiol-yne chemistry to generate biodegradable materials for biomedical applications are disclosed in International Application No. PCT/US2012/022920. Both references are hereby incorporated herein by reference in their entirety.

In some embodiments, a biomacromolecule containing single or multiple thiol groups is subjected to a photoinitiated thiol-ene or thiol-yne reaction with another molecule containing single or multiple olefin or alkyne moieties. In a preferred embodiment, a biomacromolecule is a protein. In one embodiment, a biomacromolecule (e.g., a protein such as fibrinogen) containing single or multiple thiol groups is subjected to a photoinitiated thiol-ene reaction with another molecule containing single or multiple olefin moieties, such as a molecule comprising a norbornene or vinyl ether moiety. In a particular embodiment, a biomacromolecule (e.g., a protein such as fibrinogen) is derivatized by attaching 3 or more ene containing moieties such that a fully crosslinked three-dimensional polymer network is formed. In a particular embodiment, a biomacromolecule (e.g., a protein such as fibrinogen) is derivatized by attaching 3 or more thiol containing moieties such that a fully crosslinked three-dimensional polymer network is formed. The three-dimensional polymer network can be used as a scaffold for tissue regeneration. The invention also provides products produced by the methods detailed herein.

A cross-linked three-dimensional polymer network provided herein in one embodiment is obtained by reacting a biomacromolecule (e.g., a protein such as fibrinogen) comprising n ene moieties with another molecule comprising m thiol moieties, where n and m are each independently equal to 2 or more and the sum on n and m is equal to 5 or more, such that a crosslinked three-dimensional polymer network is formed. It is understood that the biomacromolecule (e.g., a protein such as fibrinogen) comprising n ene moieties may be prepared by methods known in the art or as detailed herein. In one aspect, and as shown in Scheme 1 below, the biomacromolecule (e.g., a protein such as fibrinogen) comprising n ene moieties is prepared from a biomacromolecule comprising n thiol moieties wherein the thiol-containing biomacromolecule undergoes a thiol-ene reaction with another molecule comprising two or more ene moieties. The resulting product can then be carried forward in another thiol-ene reaction with another molecule comprising m thiol moieties (e.g., a crosslinking agent) such that a three dimensional network is provided. A polymer network may thus be obtained by a two step thiol-ene reaction wherein the first step of the reaction is directed to obtaining a macromolecule that can be taken forward in a polymerization reaction (by introducing an ene functionality to the macromolecule) and the second step of the reaction is to carry out a thiol-ene reaction with a crosslinking agent to create a three dimensional polymer network. In one aspect of the first step of such a reaction, an excess of an ene-containing compound (N-PEG-N in Scheme 1) is employed and unreacted starting material of the ene-containing compound (N-PEG-N in Scheme 1) is removed prior to carrying out the second thiol-ene reaction (purification occurs prior to step two). In one aspect step two utilizes a concentration of the crosslinking agent (HS—X—SH in Scheme 1) chosen such that the molar concentration of thiol groups provided by the crosslinking agent is equal to or approximately equal to the molar concentration of enes provided by the modified biomacromolecule. For example, if the number of ene groups on the biomacromolecule (n) is 3 and the number of thiol groups on the crosslinking agent (m) is two, then the crosslinking agent should be provided at 1.5 times the concentration of the biomacromolecule.

In another embodiment, a cross-linked three-dimensional polymer network is obtained by reacting a biomacromolecule (e.g., a protein such as fibrinogen) comprising n thiol moieties with another molecule comprising m ene moieties, where n and m are each independently equal to 2 or more and the sum of n and m is equal to 5 or more, such that a crosslinked three-dimensional polymer network is formed. It is understood that the biomacromolecule (e.g., a protein such as fibrinogen) comprising n thiol moieties may be prepared by methods known in the art or as detailed herein.

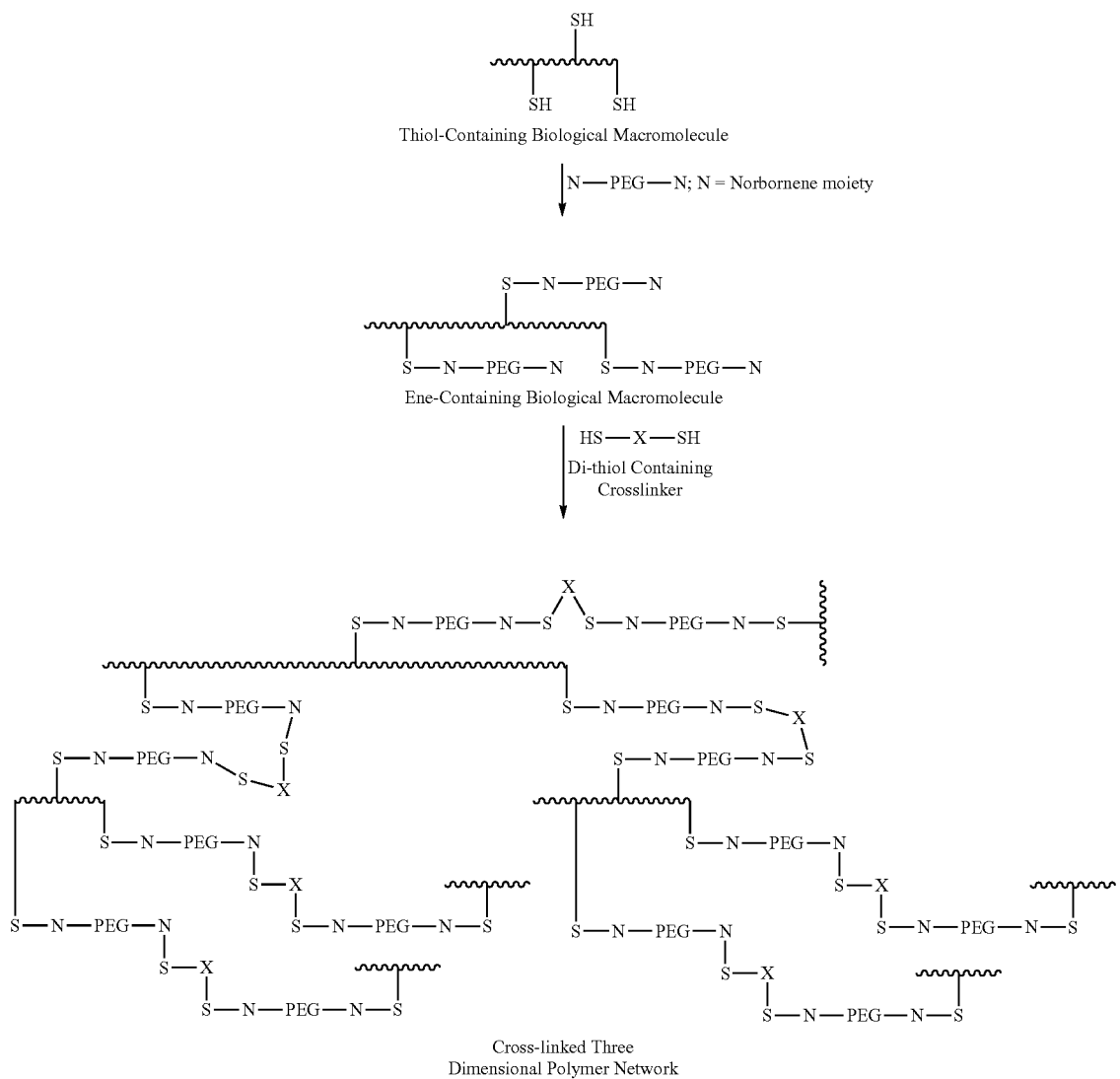

Scheme 1. Exemplary Three Dimensional Network Using Two Step thiol-Ene Transformation Thiol moieties are commonly found in proteins (cysteine side chains) and if a protein naturally exhibits a chemically accessible thiol or thiols, the thiol-ene reaction can be performed under non-denaturing conditions, at any pH and ionic strength that favors certain functional aspects of the reaction mixture, such as, for example, the solubility of the protein and/or of the other molecule. It will be recognized by one skilled in the art that certain proteins or fragments thereof may be naturally void of the cysteine residues as the result of evolutionary pressure or mutagenesis. In such cases, thiols can be introduced into the protein of interest by a variety of the biochemical techniques known in the art, for example, by converting lysine side chains into thiols via treatment with Traut's reagent, or N-succinimidyl-S-acetyl-thiopropionate (SATP), or N-Succinimidyl-S-Acetylthioac-etate (SATA) or others. Alternatively, cysteine residues can be introduced into a protein of interest by site-directed mutagenesis and the recombinant protein can be obtained by expression and purification techniques well known in the art.

In certain proteins naturally occurring cysteine residues are involved in a formation of disulfide bridges and may exhibit reduced reactivity towards thiol-ene or thiol-yne photoinitiated processes. Such disulfides can be easily converted into highly reactive thiols by treatment with reducing agents that are well known in the art, for example with tris(2-carboxyethyl)phosphine (TCEP). In certain proteins reduction of the disulfide bridge or bridges will not interfere with certain functional aspects of the protein, such as, for example, solubility, in which case reduced protein can be subjected to the thiol-ene or thiol-yne reaction directly. In other cases, protein solubility may be hampered by reduction, in which case thiol-ene reaction can be performed under non-physiological conditions that will improve protein solubility, such as, for example under highly acidic conditions (low pH) and/or in the presence of chaotropic agent such as urea, guanidinium salt or formamide. It will also be recognized that reduction of the disulfide or disulfides is not the only prerequisite of poor solubility of a protein or a fragment thereof, and that the thiol-ene or thiol-yne reaction may be performed with any such protein under said non-physiological conditions regardless of the way the thiol moiety was introduced.

In certain embodiments, it is advantageous for the protein (or other biological macromolecules) component to bear an olefin or alkyne group instead of a thiol. As disclosed herein, such modifications can be introduced into proteins by conventional biochemical techniques, for example by modifying lysine side chains to include an olefin moiety upon treatment of a protein with of N-hydroxysuccinimide ester of 5-norbornene-2-carboxylic acid or any other heterobifunctional reagent bearing ene of interest and orthogonal functionality reactive to specific chemical group presented by the protein.

The olefin or alkyne-containing moieties to be covalently crosslinked to the thiol groups by photo-initiated thiol-ene or thiol-yne chemistry are chosen with respect to the specific functional property that the modification is sought to confer, for a non-limiting example, introduction of a fluorophore or chromophore, introduction of an affinity tag, introduction of enzymatic activity, introduction of a certain chemical moiety or moieties, introduction of a hydrophilic, hydrophobic or amphiphilic polymeric tail in order to manipulate solubility, pharmacokinetics, pharmacodynamics or interaction with biological membranes or solid surfaces, generation of a protein-containing polymer or of a telechelic monomer for further polymerization etc., and may include appropriate derivatives of the following (non-limiting example): poly (lactic acid) (PLA), polyglycolide (PGA), copolymers of PLA and PGA (PLGA), poly(vinyl alcohol) (PVA), poly (ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose, hydroxyalkylated celluloses such as hydroxyethyl cellulose and methylhydroxypropyl cellulose, and natural polymers such as polypeptides, polysaccharides or carbohydrates such as polysucrose, hyaluronic acid, dextran and similar derivatives thereof, heparan sulfate, chondroitin sulfate, heparin, or alginate, and proteins such as gelatin, collagen, albumin, or ovalbumin, fibrinogen, fibrin, laminin, fibronectin, vitronectin, fluorescent proteins such as green fluorescent protein or its analogs, fluorescent and non-fluorescent dyes, fluorescence quenchers, high-affinity tags, such as polypeptide tags (His-tag, FLAG-tag and others), antibodies and fragments thereof, nucleic acid aptamers, oligonucleotides and polynucleotides, high-order macromolecular assemblies such as ribonucleoproteins, viral capsids etc.

The thiol-ene and thiol-yne reactions are discrete in nature, that is to say that one olefin moiety can react with only one thiol moiety and one alkyne moiety can react with no more than two thiol moieties. In one aspect, the thiol-ene reactions of the current invention are click-like in nature. This property allows one to control the nature of the reaction products on a number of levels. For example, a protein molecule bearing a single accessible thiol and another molecule bearing a single olefin will react to generate a single covalently linked product. If, however, one of the reagents is homo-bifunctional, for instance a mono-thiol containing protein reacting with a linear PEG-dinorbornene, two products are expected: a mono-PEGylated protein and a protein dimer crosslinked by the PEG. The relative ratio of these products can easily be controlled by manipulating stoichiometric ratio of the reactants, with mono-PEGylated protein being favored at stoichiometric excess of the PEG-dinorbornene over the mono-thiol protein, and with the crosslinked dimer being favored at the inverse stoichiometric ratio. As disclosed in the specific Examples herein, this principle holds true even in the more complicated cases, where both reactants bear two or more reactive groups in the same molecule: thiol-ene reaction of the reduced, denatured fibrinogen with excess linear PEG dinorbornene (Example 1) results predominantly in PEGylated protein that bears unnatural (norbornene) chemical groups that can be used for further modifications.

In another aspect of the current invention, proteins or other macromolecules that have been modified to bear the alkene or alkyne (either through the above methods or through other that will be known to those skilled in the art) can be subsequently crosslinked through a multi-functional thiol containing crosslinker, thereby forming a polymer network. For example, reaction between a protein bearing multiple norbornene modifications (Examples 2 and 3) and a bifunctional agent (dithiothreitol) at the 1:1 stoichiometric ratio of the thiols and enes results in a highly crosslinked, protein-containing polymeric network. In other embodiments, the bifunctional agent is a peptide containing two or more cysteine groups. The nature of the products of the thiol-ene and thiol-yne reactions can be controlled at the level of the degree of substitution of the reactants (e.g. number of the thiols and olefins or alkynes per molecule) and by the relative stoichiometry of these reactants. For example, in order to form a crosslinked thiol-ene polymer network, it is necessary that both the ene containing component and the thiol containing component have at least 2 functional groups and that the total number of functional groups be at least 5. Additional implementations will be apparent to the one skilled in the art; Examples 4 and 5 extend this notion to reactions between multi-functional protein and a mono-functional affinity tag.

Compositions comprising a modified biological macromolecule as detailed herein are also provided herein. Thus, in one aspect is provided a composition comprising a modified biological macromolecule, wherein the biological macromolecule comprises a thiol or an ene moiety prior to modification and wherein the modification comprises reacting the thiol or ene of the biological macromolecule with a mutually reactive functional group (e.g., an ene or a thiol, respectively) under free radical reaction conditions to provide the modified biological macromolecule. In one aspect of the composition, the biological macromolecule is a protein comprising a thiol moiety and wherein the modification comprises reacting the thiol-containing biological macromolecule with an ene moiety possessing click-like properties (e.g., an ene comprising a norbornene or vinyl ether moiety) under free radical reaction conditions. Thus, in one aspect is provided a modified biological macromolecule wherein the modification is achieved by reacting a thiol group on the biological macromolecule with a compound comprising a click-like ene moiety, such as a norbornene or vinyl ether containing compound (e.g., a PEG group modified to contain a norbornene moiety). Likewise, also provided is a composition comprising a modified biological macromolecule wherein the biological macromolecule is a protein comprising an ene moiety possessing click-like properties (e.g., a protein derived to comprise a norbornene or vinyl ether moiety) and wherein the modification comprises reacting the ene-containing biological macromolecule with a thiol moiety under free radical reaction conditions. Thus, in one aspect is provided a modified biological macromolecule wherein the modification is achieved by reacting a click-like ene moiety on the biological macromolecule, such as a norbornene or vinyl ether containing moiety on the biological macromolecule, with a thiol containing compound (e.g., a PEG group modified to contain a thiol moiety).

Also provided herein is a three-dimensional scaffold for biomedical use (e.g., a scaffold for use in tissue regeneration). In one aspect, the three-dimensional scaffold comprises a modified biological macromolecule wherein the biological macromolecule comprises at least two or three thiol or ene moieties and wherein the modification comprises reacting the at least two or three thiol or ene moieties of the biological macromolecule with a compound comprising at least two or three mutually reactive functional groups (e.g., ene or a thiol groups, respectively) under free radical reaction conditions to provide the three-dimensional scaffold. It is understood that, as illustrated in Scheme 1, the biological macromolecule for carrying forward in the polymerization reaction may be prepared by methods known in the art or as detailed herein, such as by utilizing a first thiol-ene reaction with a thiol-containing biological macromolecule to introduce free ene moieties that may subsequently be used in a polymerization reaction with a thiol containing crosslinker to provide a three dimensional polymer network. In one aspect, a three-dimensional scaffold is provided, wherein the scaffold comprises a modified biological macromolecule wherein the biological macromolecule is a protein comprising at least two or three thiol moieties and wherein the modification comprises reacting the thiol-containing protein with a compound comprising at least two or three ene moieties possessing click-like properties (e.g., with a compound comprising two or three norbornene or vinyl ether moieties) under free radical reaction conditions, thereby providing the three-dimensional scaffold. Also provided is a three-dimensional scaffold, wherein the scaffold comprises a modified biological macromolecule wherein the biological macromolecule is a protein comprising at least two or three click-like ene moieties (e.g., a protein comprising two or three norbornene or vinyl ether moieties) and wherein the modification comprises reacting the ene-containing protein with a compound comprising at least two or three thiol moieties under free radical reaction conditions, thereby providing the three-dimensional scaffold.

Methods of using the scaffolds provided herein for tissue regeneration are also provided. In one aspect, the method comprises contacting a tissue with a scaffold provided herein under conditions conducive to tissue growth. In one aspect is provided a method of healing a wound comprising contacting a wound with a scaffold provided herein, wherein the scaffold provides three dimensional structure to aid with tissue regeneration. In one aspect is provided a method of healing a wound comprising contacting a wound with the starting materials for a scaffold as provided herein (e.g., contacting the wound with a thiol- or ene-derived protein and with a mutually reactive other molecule so that the protein and other molecules are capable of undergoing a thiol-ene reaction) under conditions suitable for free radical polymerization. In one aspect, the method comprises containing the wound with the scaffold starting materials as detailed herein and photoinitiating a free radical reaction to produce a scaffold to aid in tissue regeneration.

Enumerated Embodiments

The following enumerated embodiments are embraced by the present invention.

Embodiment 1. A method of covalently modifying a biological macromolecule, the method comprising subjecting a reaction mixture comprising: (a) a biological macromolecule comprising one or more thiol groups; and (b) a molecule comprising one or more olefin moieties possessing click-like properties to a radical reaction under conditions sufficient to produce the covalently modified biological macromolecule.

Embodiment 2. The method of embodiment 1, wherein the biological macromolecule is a protein.

Embodiment 3. The method of embodiment 1 or 2, wherein the radical reaction is a photoinitiated radical reaction.

Embodiment 4. The method of any one of embodiments 1 to 3, wherein the radical reaction is performed under non-denaturing conditions.

Embodiment 5. The method of any one of embodiments 1 to 4, wherein the olefin comprises either a norbornene or a vinyl ether moiety.

Embodiment 6. The method of any one of embodiments 1 to 5 where the reaction is essentially completed within 10 or 5 or 2 or 1 minutes of radical initiation.

Embodiment 7. The method of any one of embodiments 1 to 6, wherein the biological macromolecule comprises one or more lysine side chains, and wherein the one or more thiol groups are introduced into the biological macromolecule by converting the one or more lysine side chains into the one or more thiol groups.

Embodiment 8. The method of any one of embodiments 1 to 6, wherein the one or more thiol groups are introduced into the biological macromolecule by site directed mutagenesis.

Embodiment 9. The method of any one of embodiments 1 to 6, wherein the biological macromolecule comprises one or more disulfide bonds, and wherein the one or more thiol groups are introduced into the biological macromolecule by converting the one or more disulfide bonds into the one or more thiol groups.

Embodiment 10. The method of any one of embodiments 1 to 9, wherein the one or more olefin containing moieties further comprises one or more groups selected from the group consisting of poly(lactic acid) (PLA), polyglycolide (PGA), copolymer of PLA and PGA (PLGA), poly(vinyl alcohol) (PVA), poly(ethylene glycol) (PEG), poly(ethylene oxide), poly(ethylene oxide)-co-poly(propylene oxide) block copolymer (poloxamers, meroxapols), poloxamine, polyanhydride, polyorthoester, poly(hydroxy acid), polydioxanone, polycarbonate, polyaminocarbonate, poly(vinyl pyrrolidone), poly(ethyl oxazoline), carboxymethyl cellulose, hydroxyalkylated cellulose, hydroxyethyl cellulose, and methylhydroxypropyl cellulose.

Embodiment 11. The method of any one of embodiments 1 to 9, wherein the one or more olefin containing moieties further comprises one or more groups selected from the group consisting of polypeptide, polysaccharide, carbohydrate, polysucrose, hyaluranic acid, dextran, dextran derivative, heparan sulfate, chondroitin sulfate, heparin, and alginate.

Embodiment 12. The method of any one of embodiments 1 to 9, wherein the one or more olefin moieties further comprises one or more groups selected from the group consisting of gelatin, collagen, albumin, ovalbumin, fibrinogen, fibrin, laminin, fibronectin, vitronectin, fluorescent protein, green fluorescent protein, fluorescent dye, non-fluorescent dye, fluorescence quencher, polypeptide tag, His-tag, FLAG-tag, antibody, antibody fragment, nucleic acid aptamer, oligonucleotide and polynucleotide, ribonucleoprotein, and viral capsids.

Embodiment 13. The method of any one of embodiments 1 to 6, wherein the biological macromolecule is fibrinogen.

Embodiment 14. The method of any one of embodiments 1 to 6, wherein the biological macromolecule is chymopapain.

Embodiment 15. A method of covalently modifying a biological macromolecule, the method comprising subjecting a reaction mixture comprising: (a) a molecule comprising one or more thiol groups; and (b) a biological macromolecule comprising one or more olefin moieties possessing click-like properties to a radical reaction under conditions sufficient to produce the covalently modified biological macromolecule.

Embodiment 16. The method of embodiment 15, wherein the biological macromolecule is a protein.

Embodiment 17. The method of embodiments 15 or 16, wherein the radical reaction is a photoinitiated radical reaction.

Embodiment 18. The method of any one of embodiments 15 to 17, wherein the radical reaction is performed under non-denaturing conditions.

Embodiment 19. The method of any one of embodiments 15 to 18, wherein the biological macromolecule is fibrinogen.

Embodiment 20. The method of any one of embodiments 15 to 18, wherein the biological macromolecule is chymopapain.

Embodiment 21. The method of embodiments 15 to 20 where the olefin comprises either a norbornene or a vinyl ether moiety.

Embodiment 22. The method of embodiments 15 to 21 where the reaction is essentially completed within 10 or 5 or 2 or 1 minutes of radical initiation.

Embodiment 23. The covalently modified biological macromolecule prepared according to the method of embodiments 1-22.

The following examples are offered to illustrate provided embodiments and are not intended to limit the scope of the invention.

EXAMPLES

Example 1

Preparation of PEGylated Fibrinogen Bearing Reactive Norbornene Moieties

Bovine fibrinogen (MP Biomedicals) was denatured by dissolving in 8M urea, 1×PBS buffer pH 7.4 (Thermo Scientific) at 30 mg/mL at ambient temperature. In order to convert oxidized Cysteine residues into free thiols, fibrinogen solution was then treated with a reducing agent TCEP-HC1 (Thermo Scientific; 100 mg per 1 g protein or ~2:1 molar ratio of TCEP to Cysteine residues in the protein, based on molecular weight and sequence of bovine fibrinogen available at uniprot.org) for 10 min to 1 hour at ambient temperature. Optionally, pH of the protein solution can be lowered after this step to 4-5, for example by titration with acid or by dialysis against 8M urea in phosphate buffer at pH 4-5, in order to improve solubility of reduced, denatured fibrinogen at subsequent steps and to minimize undesirable reactivity of free thiols (e.g. towards formation of S—S bonds upon exposure to air).

Reduced, denatured fibrinogen solution was then placed into a transparent glass Reaction Vessel (e.g. a 250 mL conical flask) equipped with a stir bar and stirred with a magnetic stirrer. Solution of poly(ethylene glycol) dinorbornene (NB-PEG-NB; average MW 3.4 kDa) at concentration 140 mg/mL in 6 M urea was added drop-wise to the reduced denatured protein solution upon stirring (7 g NB-PEG-NB per 1 g fibrinogen, or molar ratio of ~12:1 of NB-PEG-NB to Cysteines), followed by addition of photo-initiator lithium phenyl-2,4,6-trimethylbenzoylphosphinate (LiAP) to final concentration of 0.5 mg/mL.

The reaction mixture was then irradiated with 385 nm light (ThorLabs M385L2-C2) at 2 mW/cm$^2$ (11.2 cm$^2$ total irradiated area) for 3 min upon vigorous stirring. In independent experiments this dose of light was found sufficient to convert all free thiols in the reaction mixture into the products of photo-initiated thiol-ene reaction given specific configuration of Reaction Vessel and concentrations and amounts of reagents used. Optionally, the progress of the reaction can be monitored, for example, by monitoring consumption of free thiols over irradiation time, as determined by Ellman's test that is well known in the art (it is advised that the unreacted TCEP in such case is removed from reduced, denatured fibrinogen prior to photo-induced PEGylation step, for example by dialysis as described above).

Unreacted NB-PEG-NB was subsequently removed by extensive diafiltration against 6 M urea in a stirred pressure cell (Millipore) equipped with a 100 kDa Molecular Weight Cut-Off ultrafiltration membrane (Millipore). Denatured PEGylated fibrinogen was refolded by extensive dialysis against 1×PBS plus 0.1 volume % glacial acetic acid at 4° C. over a period of a few days with buffer replaced twice daily. Optionally, the protein can be desalted at this step by additional dialysis against water. Refolded PEGylated fibrinogen was concentrated with centrifugal filter devices (Centriprep YM 50; Millipore) to a final concentration of ~120*10-6 M (determined by absorbance at 280 nm in 8M urea, 1×PBS pH 7.4 with the extinction coefficient of 5.2*105 $M^{-1}*cm^{-1}$ that was calculated for fibrinogen hexamer from the protein sequence available at uniprot.org). Concentration of the attached reactive norbornene in the stock solution of modified protein was estimated with a thiol consumption test, where various concentrations of the modified protein in the presence of 1 mM cysteine hydrochloride and 0.05% LiAP were irradiated in an optically thin sample with 385 nm light at 2 mW/cm2 for one minute (time sufficient to drive thiol-ene reaction to completion under these conditions), concentration of remaining cysteine was determined by Ellman's test and the concentration of remaining thiol was plotted against concentration of the protein in the irradiated sample; this plot displayed negative linear relationship and the negative slope of this line (determined by linear regression analysis) was interpreted as concentration of norbornene per concentration of protein in the stock solution (3.9 mM norbornene per 43.3 mg/mL protein, or approximately 30 norbornene residues per fibrinogen hexamer).

Example 2

Covalent Incorporation of Norbornene Moieties into a Protein Under Non-Denaturing Conditions 302 milligrams of bovine fibrinogen (MP Biomedicals) were dissolved in 10 mL of the buffer containing 50 mM HEPES-Na, 100 mM NaCl, 0.25 mM EDTA, pH 8.0 and dialyzed overnight in a 12 mL Slide-A-Lyzer cassette, MWCO 10 kDa (Thermo Scientific) against 1 L of the same buffer in order to remove potential low-molecular weight contaminants.

In a dry, argon-purged 100 mL round-bottom flask equipped with a Teflon-coated stir bar 40 microliters (0.33 mmol) of 5-norbornene-2-carboxylic acid dissolved in 3 mL of anhydrous acetonitrile was combined with 25 microliters (0.33 mmol) of anhydrous pyridine and 105 mg of N,N'-disuccinimidyl carbonate (0.41 mmol). The reaction was stirred for 3 hours at ambient temperature under constant argon flow, at which point the solvent was removed by evaporation at reduced pressure. The crude N-hydroxysuccinimide ester of 5-norbornene-2-carboxylic acid was dissolved in 1 mL of anhydrous dimethylformamide to furnish approximately 0.3 M.

To the 2.5 mL aliquots of dialyzed fibrinogen solution in 15 mL conical tubes 20 microliters (treatment A) or 40 microliters (Treatment B) of the 0.3 M solution of N-hydroxysuccinimide ester of 5-norbornene-2-carboxylic acid in dimethylformamide were added and the resulting solutions were thoroughly mixed by vortexing for 30 seconds. Following incubation at ambient temperature for 35 minutes, another 20 (Treatment A) or 40 microliters (Treatment B) of the 0.3 M solution of N-hydroxysuccinimide ester of 5-norbornene-2-carboxylic acid in dimethylformamide were added, reaction mixtures were vortexed for 30 seconds again and left at ambient temperature for another 2 hours. Small amount of insoluble material formed in the course of the treatments was removed by centrifugation, and the modified protein was extensively dialyzed at ambient temperature against phosphate-buffered saline (PBS; pH 7.4) in 3 mL Slide-A-Lyzers MWCO 3.5 kDa in order to remove low-molecular weight products of the reaction.

Concentration of the product protein was determined spectrophotometrically, and concentration of available norbornene was estimated by thiol consumption test as disclosed in the Example 2 above. For Treatment A, 0.65 mM norbornene per 17.8 mg/mL product protein was detected (16 norbornene residues per fibrinogen hexamer) and for Treatment B 1.46 mM norbornene per 16.7 mg/mL protein was detected (29 norbornene residues per fibrinogen hexamer).

To confirm covalent attachment of norbornene to protein, 100 microliters of protein from Treatment B (16.7 mg/mL protein; 1.46 mM norbornene) was mixed with 12 microliters of 3% PEG dithiol 5 kDa (JenKem Technology USA; stoichiometric ratio of norbornene to thiol), 3 microliters of 2% LiAP in water were added and resulting solution was irradiated with 385 nm light at 2 $mW/cm^2$ for one minute in a cylindrical rubber mold. Fast hydrogel formation was observed, confirming covalent attachment of norbornene residues to the protein.

Example 3

Covalent Incorporation of a Protein into a Hydrogel Scaffold by Thiol-ene Chemistry 100 microliter samples containing 20 mg/mL of PEGylated fibrinogen bearing norbornene residues (disclosed in Example 1 above), 0.06 wt % LiAP and 0.9 mM dithiothreitol (approximately sthoichiomertic ratio of norbornene to thiol) were prepared. In situ photopolymerization was followed in a fast oscillation time sweep tests on gelling solutions in a parallel-plate shear rheometer (TA Instruments Discovery HR-3; 8.0 mm diameter and 0.25 mm height). Time sweep tests were conducted at 6 rad/s with 1% strain, which was determined to be in the linear viscoelastic regime for both chain and step polymerized hydrogels. Polymerization was initiated 5 s after the start of time sweep experiment by a 365 nm light at 3 $mW/cm^2$ that was directed through a flat quartz plate through the sample. Polymerization was followed until the shear storage modulus (G') reached a plateau (FIG. 1A). Close inspection of the data reveals that shear storage (G') and loss (G") moduli cross over within about 7 seconds of irradiation, indicating a fast liquid to solid transition; polymerization is complete within 3 minutes of irradiation (G' reaches plateau).

Covalent incorporation of the protein into a hydrogel was confirmed by trypsin digestion experiment. 75 microliter aliquots of 50 mg/mL PEGylated fibrinogen bearing norbornene residues (disclosed in Example 2 above), 0.05 wt % LiAP and 2.25 mM dithiothreitol (approximately sthoichiometric ratio of norbornene to thiol) were photopolymerized in cylindrical plastic molds (5 mm diameter). One hydrogel cylinder was then immersed into 1 mL of 0.05% Trypsin in DMEM media (Cellgro) and another into 1 mL of phosphate-buffered saline (PBS, pH 7.4) and both were incubated at 37° C. for 3 hours 30 min, at which point the liquid was removed from each sample and remaining hydrogels were inspected visually. As illustrated in FIG. 1B, treatment with trypsin resulted in almost complete dissolution of the hydrogel plug, confirming that modified fibrinogen was indeed covalently incorporated into the hydrogel as the part of the backbone.

Example 4

Addition of Primary Functional Moiety (Protein-C—C—S-Linker-Biotin)

The non-denatured, norbornylated fibrinogen derivative disclosed in the Example 2 above (Treatment A) dissolved in phosphate-buffered saline at a concentration of 1 mg/mL (48 micromolar norbornene) is supplemented with LiAP at 0.05 wt % and 32 mg/mL biotinylated tri(ethylene glycol) undecane thiol (NanoScience Instruments; 50 micromolar thiol) and placed into a UV-transparent cuvette of appropriate size (preferably, with an optical path length of 1-2 cm). The solution is irradiated at 365-400 nM (preferably, 385 nM) at 2 mW/cm$^2$ for the time period sufficient to drive thiol-ene reaction to completion (the progress of the reaction can be monitored, for example, by monitoring consumption of free thiols over irradiation time, as disclosed in the Example 2 above). If desired, the product protein is extensively dialyzed against a buffer suitable for downstream applications.

Example 5

Addition of Secondary Functional Moiety (Protein-S—C—C-Linker-C—C—S-Biotin)

The PEGylated, norbornene-bearing fibrinogen disclosed in the Example 1 above dissolved in phosphate-buffered saline at a concentration of 1 mg/mL (90 micromolar norbornene) is supplemented with LiAP at 0.05 wt % and 58 mg/mL biotinylated tri(ethylene glycol) undecane thiol (NanoScience Instruments; 50 micromolar thiol) and placed into a UV-transparent cuvette of appropriate size (preferably, with an optical path length of 1-2 cm). The solution is irradiated at 365-400 nM (preferably, 385 nM) at 2 mW/cm$^2$ for the time period sufficient to drive thiol-ene reaction to completion (the progress of the reaction can be monitored, for example, by monitoring consumption of free thiols over irradiation time, as disclosed in the Example 2 above). If desired, the product protein is extensively dialyzed against a buffer suitable for downstream applications.

Example 6

PEGylation of a Protein Under Non-Denaturing Conditions

Chromatographically purified chymopapain (available from Sigma) is dissolved in 0.1 M sodium acetate buffer (pH 5.0) at 0.1 mg/mL concentration (~8.5 micromolar concentration of free thiols) and solution is supplemented with linear PEG-dinorbornene 3.5 kDa at a final concentration of 1 wt % (5.7 mM norbornene) and LiAP at 0.04 wt %. The solution is placed into a UV-transparent cuvette of appropriate size (preferably, with an optical path length of 1-2 cm) and irradiated at 365-400 nM (preferably, 385 nM) at 2 mW/cm$^2$ for the time period sufficient to drive thiol-ene reaction to completion. If desired, PEGylated protein is purified from unreacted PEG-dinorbornene by conventional chromatographic techniques or by diafiltration.

All references, including patents, patent applications and journal articles, are hereby incorporated herein by reference in their entirety.

We claim:

1. A covalently modified fibrinogen protein or fibrinogen fragment thereof comprising a —S—N-moiety, wherein the covalently modified fibrinogen protein or fibrinogen fragment thereof is prepared by a method comprising:
   (I) subjecting a fibrinogen protein or fibrinogen fragment to denaturing and reducing conditions to produce a reduced, denatured fibrinogen protein or a denatured fibrinogen fragment comprising one or more thiol groups;
   (II) reacting the reduced, denatured fibrinogen protein or fibrinogen fragment with one or more norbornene moieties under conditions to promote radical initiation and produce a photoinitiated radical thiol-ene coupling reaction between at least one of the one or more norbornene moieties and at least one of the one or more thiol groups on the reduced, denatured fibrinogen protein or fibrinogen fragment, thereby providing the covalently modified fibrinogen protein or fibrinogen fragment,
   wherein the S of the —S—N-moiety corresponds to the sulfur atom of the thiol group of one of the one or more thiol groups of the reduced, denatured fibrinogen protein or fibrinogen fragment;
   wherein the N of the —S—N-moiety corresponds to the hydrothiolated norbornene moiety obtained from the one or more norbornene moiety; and
   wherein the one or more norbornene moieties comprise a polymer selected from the group consisting of:
   poly (lactic acid) (PLA), polyglycolide (PGA), copolymer of PLA and PGA (PLGA), poly (vinyl alcohol) (PVA), poly (ethylene glycol) (PEG), poly (ethylene oxide), poly (ethylene oxide)-co-poly(propylene oxide) block copolymer, poloxamine, polyanhydride, polyorthoester, poly(hydroxy acid), polydioxanone, polycarbonate, polyaminocarbonate, poly(vinyl pyrrolidone), poly (ethyl oxazoline), carboxymethyl cellulose, hydroxyalkylated cellulose, polysucrose, hyaluronic acid, dextran, heparan sulfate, chondroitin sulfate, heparin, and alginate.

2. The covalently modified fibrinogen protein or fibrinogen fragment of claim 1, wherein the polymer is poly (ethylene glycol) (PEG).

3. The covalently modified fibrinogen protein or fibrinogen fragment of claim 1, wherein the one or more norbornene moieties is a linear PEG-dinorbornene.

4. The covalently modified fibrinogen protein or fibrinogen fragment of claim 3, wherein the linear PEG-dinorbornene has an average molecular weight of 3.4 kDa.

5. The covalently modified fibrinogen protein or fibrinogen fragment of claim 3, wherein the reduced, denatured fibrinogen protein or fibrinogen fragment is reacted with a stoichiometric excess of linear PEG-dinorbornene.

6. The covalently modified fibrinogen protein or fibrinogen fragment of claim 5, wherein the method comprises attaching 3 or more linear PEG-dinorbornene to the reduced, denatured fibrinogen protein or fibrinogen fragment.

7. The covalently modified fibrinogen protein or fibrinogen fragment of claim 1, wherein the denaturing conditions comprise dissolving the fibrinogen protein or fibrinogen fragment in a buffered urea solution.

8. The covalently modified fibrinogen protein or fibrinogen fragment of claim 1, wherein the reducing conditions comprise treatment with tris(2-carboxyethyl)phosphine.

9. The covalently modified fibrinogen or fibrinogen fragment protein of claim 8, wherein the method further comprises removing unreacted tris(2-carboxyethyl)phosphine from the reduced, denatured fibrinogen protein or fibrinogen fragment prior to step (II).

10. The covalently modified fibrinogen protein or fibrinogen fragment of claim 1, wherein the conditions to promote radical initiation and to produce the photoiniated radical thiol-ene coupling reaction comprise a photo-initiator.

11. The covalently modified fibrinogen protein or fibrinogen fragment of claim 10, wherein the photo-initiator is lithium phenyl-2,4,6-trimethylbenzoylphosphinate.

12. The covalently modified fibrinogen protein or fibrinogen fragment of claim 1, wherein the photoinitiated radical thiol-ene coupling reaction is essentially completed within 5 minutes of radical initiation.

13. The covalently modified fibrinogen protein or fibrinogen fragment of claim 1, wherein the photoinitiated radical thiol-ene coupling reaction is essentially completed within 1 minute of radical initiation.

14. The covalently modified fibrinogen protein or fibrinogen fragment of claim 1, wherein the conditions to promote radical initiation and to produce the photoiniated radical thiol-ene coupling reaction comprise irradiating with light at a wavelength of 385 nm.

15. The covalently modified fibrinogen protein or fibrinogen fragment of claim 1, further comprising refolding the covalently modified fibrinogen protein or fibrinogen fragment.

* * * * *